United States Patent [19]

Ishikawa et al.

[11] Patent Number: 4,983,757

[45] Date of Patent: Jan. 8, 1991

[54] PROCESS FOR PRODUCTION OF CARBOXYLIC ACID ESTERS AND FORMAMIDE

[75] Inventors: Jiro Ishikawa; Hirofumi Higuchi; Shuji Ebata; Koichi Kida, all of Niigata, Japan

[73] Assignee: Mitsubishi Gas Chemical Company, Inc., Tokyo, Japan

[21] Appl. No.: 500,520

[22] Filed: Mar. 28, 1990

[30] Foreign Application Priority Data

Apr. 11, 1989 [JP] Japan .................................. 1-89737

[51] Int. Cl.$^5$ ..................... C07C 69/76; C07C 233/00
[52] U.S. Cl. .................................. 560/103; 560/155; 560/179; 560/217; 560/234; 560/265; 564/215; 546/319; 546/318
[58] Field of Search .............. 560/103, 265, 234, 155, 560/179, 217; 564/215

[56] References Cited

U.S. PATENT DOCUMENTS 2,413,889  1/1947  Rehberg et al. ..................... 560/234
3,784,573  1/1974  Fields ................................. 560/234

FOREIGN PATENT DOCUMENTS 313316  6/1929  United Kingdom .
922953  4/1983  United Kingdom .

Primary Examiner—Paul J. Killos
Attorney, Agent, or Firm—Frishauf, Holtz, Goodman & Woodward

[57] ABSTRACT

Carboxylic acid esters and formamide are efficiently obtained for reacting carboxylic acid amides and formic acid esters, or carboxylic acid amides, alcohols and carbon monoxide in the presence of an alkaline earth metal oxide catalyst.

14 Claims, No Drawings

PROCESS FOR PRODUCTION OF CARBOXYLIC ACID ESTERS AND FORMAMIDE

BACKGROUND OF THE INVENTION

1. Field of the Invention

The present invention relates to a process for efficient production of carboxylic acid esters and formamide by reacting carboxylic acid amides and formic acid esters, or by reacting carboxylic acid amides, alcohols, and carbon monoxide.

2. Description of the Related Arts

Carboxylic acid esters are industrially important compounds. As methods of producing carboxylic acid esters from carboxylic acid amides, (1) a method of producing methyl acetate from acetic acid amide, (2) a method of producing methyl methacrylate from methacrylic acid amide, (3) a method of producing methyl acrylate from acrylic acid amide, and (4) a method of producing methyl α-hydroxyisobutyrate from α-hydroxyisobutyric acid amide are known.

Formamide is used as a solvent, a treating agent, an electrolyte, or an antifreezing agent, or as an intermediate for production of dyes, pigments, medicines and so on. Moreover formamide is an important basic chemical compound which can be used also as a starting material for production of hydrogen cyanide.

For production of carboxylic acid esters from carboxylic acid amides, a method of reacting carboxylic acid amides and alcohols in the presence of sulfuric acid has heretofore been known, and this method is widely employed for industrial production of methyl methacrylate.

This method, however, has disadvantages in that a large amount of acidic ammonium sulfate results as a by-product, leading to a marked increase in production costs owing to its disposal, and an expensive corrosion-resistant apparatus is also required.

In order to overcome the above problems, a method of producing carboxylic acid esters by catalytic reaction of carboxylic acid amides and alcohols without sulfuric acid has been proposed.

This method, however, has disadvantages in that yield and selectivity of the desired carboxylic acid ester are low, a large amount of ammonia is formed and requires separation and recovery, and an ammonium salt of carboxylic acid is also formed. Thus the method is not satisfactory in commercial practice thereof.

As a method not accompanied by formation of ammonia, Japanese Patent Application Laid-Open Nos. 55444/1983 and 78937/1985 disclose a method of producing carboxylic acid ester and formamide by reacting carboxylic acid amide and formic acid ester in the presence of a catalyst comprising an organic or inorganic acid metal salt, or a metal carbonyl compound, and a nitrogen or phosphorus-containing organic compound.

These methods, however, have problems that the catalyst system is complicated and expensive, and catalyst recovery costs are high.

SUMMARY OF THE INVENTION

An object of the present invention is to provide a process for producing carboxylic acid esters and formamide from carboxylic acid amides and formic acid esters with high efficiency under mild conditions.

Another object of the present invention is to provide a highly efficient process for producing carboxylic acid esters and formamide at a low production cost using an inexpensive apparatus instead of an expensive corrosion-resistant apparatus.

The present invention relates to a process for production of carboxylic acid esters and formamide by reacting carboxylic acid amides and formic acid esters (or alcohols and carbon monoxide) in the presence of alkaline earth metal oxide.

DESCRIPTION OF PREFERRED EMBODIMENTS

Carboxylic acid amides to be used in the present invention include aliphatic or aromatic carboxylic acid amides, and α-hydroxy or α-aminocarboxylic acid amides. These amides can be prepared by hydrolizing nitriles, or by reacting amines and carbon monoxide. Specific examples are acetamide, lactic acid amide, acrylic acid amide, methacrylic acid amide, α-hydroxyisobutyric acid amide, benzamide, valine amide and alanineamide.

Alcohols to be used in the present invention are preferably aliphatic alcohols having 1 to 10 carbon atoms. Formic acid esters are preferably esters of the above alcohols and formic acid. Specific examples of the aliphatic alcohols are methanol, ethanol, 1-propanol, 2-propanol, 1-butanol, 2-butanol, and 1-pentanol. Specific examples of formic acid esters are methyl formate, ethyl formate, propyl formate, isopropyl formate, n-butyl formate, sec-butyl formate, and n-pentyl formate.

As the alkaline earth metal oxide to be used in the process of the present invention, one or more compounds selected from the oxides of magnesium, calcium, strontium and barium are used. These alkaline earth metal oxides are produced by calcining hydroxide of alkaline earth metals, or inorganic acid salts, such as carbonates or nitrates, of alkaline earth metals, or organic acid salts, such as carboxylic acid salts, of alkaline earth metals at 300° to 1,500° C. Also they can be obtained by calcining the alkaline earth metal carbide, or by adding water to the alkaline earth metal carbide.

In the process of the present invention, when formic acid ester is used as the starting material, it is desirable to use a suitable solvent, because carboxylic acid amide is generally in a solid state at room temperature.

As the solvent, a polar solvent, e.g., alcohols, is preferably used. It is particularly preferred to use an alcohol constituting the formic acid ester.

When alcohol and carbon monoxide are used in place of formic acid ester as the starting materials, it is preferred that the alcohol is used in an excess amount so that it also functions as a solvent for carboxylic acid amide.

In the reaction of carboxylic acid amide and formic acid ester in the process of the present invention, the amount of the formic acid ester used is 1 to 15 mol, preferably 2 to 8 mol per mol of the carboxylic acid amide.

IN the reaction of carboxylic acid amide, alcohol and carbon monoxide in the process of the present invention, the amount of the alcohol used is 1 to 30 mol, preferably 3 to 20 mol per mol of the carboxylic acid amide.

In the present invention, carboxylic acid amide can be reacted with formic acid ester, alcohol and carbon monoxide. In this case, the amounts of formic acid ester and alcohol used are 0.5 to 15 mol and 0.5 to 30 mol, preferably 1 to 8 mol and 2 to 15 mol, respectively, per mol of carboxylic acid amide.

In the process of the present invention, the amount of alkaline earth metal oxide used is preferably 0.001 to 0.3 mol per mol of carboxylic acid amide, with the range of 0.003 to 0.2 mol being particularly preferred.

The reaction temperature and period of time can be chosen from a wide range depending on the kind of the starting material, the amount of the catalyst charged, and the conversion objective. In general, the reaction temperature is preferably 0° to 200° C. and more preferably 20° to 150° C. If the reaction temperature is less than 0° C., a practical rate of reaction can be obtained, and if it is more than 200° C., decomposition of formamide and deactivation of the catalyst occur. The reaction time is preferably 0.1 to 20 hours and particularly preferably 0.2 to 10 hours.

In connection with the reaction pressure in the reaction of carboxylic acid amide and formic acid ester in the present invention, although the reaction may be carried out under a vapor pressure at the reaction temperature, it can also be carried out under a pressure of carbon monoxide in order to prevent decomposition of formic acid ester. Specifically, the reaction pressure should be between atmospheric pressure and 300 atm, and from an economic standpoint, it is preferably between atmospheric pressure and 200 atm.

In the reaction of carboxylic acid amide, alcohol and carbon monoxide, the reaction pressure is in a range of 10 to 500 atm, preferably 30 to 400 atm as a partial pressure of carbon monoxide.

In the process of the present invention, the alkaline earth metal oxide can be used as a homogeneous catalyst by dissolving it in the starting material or a suitable solvent. The alkaline earth metal oxide can be also used as a heterogeneous catalyst, for example, as a powder in a slurry form, or as a fixed bed catalyst, such as in a carrier deposited form or a molded tablet form.

The process of the present invention can be carried out batchwise or continuously. Industrially a continuous process is preferred.

The reaction of the present invention is an equilibrium reaction. When the alkaline earth metal oxide is used in a slurry form or as a homogeneous catalyst, it is necessary to quickly separate or deactivate the catalyst after the reaction. Separation of the alkaline earth metal oxide catalyst can be easily conducted by filtration, and deactivation of the alkaline earth metal catalyst can be easily conducted by addition of an inorganic or organic acidic substance. In the latter case, the alkaline earth metal oxide can be deactivated by changing it into the corresponding hydroxide by adding water.

The catalyst once deactivated as the nitrate, carbonate or carboxylate of alkaline earth metal, or as the hydroxide of alkaline earth metal can be reproduced and reactivated into the original alkaline earth metal oxide catalyst by calcining at 300° to 1500° C.

In accordance with the process of the present invention, carboxylic acid esters and formamide can be produced with high selectivity under mild reaction conditions from carboxylic acid amides and formic acid esters by the use of alkaline earth metal oxide as a catalyst. Thus the process of the present invention is of great significance from an industrial standpoint.

The present invention is described in greater detail with reference to the following examples, although it is not intended to be limited thereto.

EXAMPLE 1

7.22 g (0.07 mol) of α-hydroxyisobutyric acid amide was placed in a 120-milliliter stainless steel autoclave, and 12.6 g (0.21 mol) of methyl formate and 6.37 g (0.21 mol) of methanol were added and dissolved therein. Then, 0.20 g (0.0036 mol) of calcium oxide was added and suspended. The reaction was carried out at a temperature of 80° C. for 2 hours.

The autoclave was cooled to 10° C., and then the product was taken out thereof and was subjected to a gas chromatographic analysis.

The conversion of α-hydroxyisobutyric acid amide was 65.2 %, and the selectivity into methyl α-hydroxyisobutyrate was 9.2%.

The selectivity into formamide (based on the reacted α-hydroxyisobutyric acid amide) was 99.3%.

EXAMPLE 2

The procedure of Example 1 was repeated with the exception that 2.95 g (0.05 mol) of acetamide was used as the carboxylic acid amide.

The conversion of acetamide was 78.6%, the selectivity into methyl acetate was 98.0%, and the selectivity into formamide was 98.4%.

EXAMPLE 3

The procedure of Example 1 was repeated with the exception that 4.25 g (0.05 mol) of methacrylic acid amide was used as the carboxylic acid amide.

The conversion of methacrylic acid amide was 76.6%, the selectivity into methyl methacrylate was 93.2%, and the selectivity into formamide was 95.5%.

EXAMPLE 4

The procedure of Example 1 was repeated with the exception that 6.11 g (0.05 mol) of nicotinic acid was used as the carboxylic acid amide.

The conversion of nicotinic acid amide was 62.4%, the selectivity into methyl nicotinate was 92.4%, and the selectivity into formamide was 93.5%.

EXAMPLE 5

The procedure of Example 1 was repeated with the exception that 51 g (0.5 mol) of butyl formate was used in place of methyl formate, and 22.2 g (0.3 mol) of butanol was used as the alcohol.

The conversion of α-hydroxyisobutyric acid amide was 75.5%, the selectivity into butyl α-hydroxyisobutyrate was 94.7%, and the selectivity into formamide was 92.2%.

EXAMPLE 6

The procedure of Example 1 was repeated with the exception that 2.3 g (0.015 mol) of barium oxide was used in place of the calcium oxide.

The conversion of α-hydroxyisobutyric acid amide was 58.6%, the selectivity into metyl α-hydroxyisobutyrate was 92.6%, and the selectivity into formamide was 94.5%.

EXAMPLE 7

In the same autoclave as used in Example 1, a solution of 7.22 g (0.07 mol) of α-hydroxyisobutyric acid amide and further 0.11 g (0.002 mol) of caluium oxide dissolved in 8.97 g (0.28 mol) of methanol, and 12.6 g (0.21 mol) of methyl formate were placed, and they were then reacted at 40° C. for 3 hours.

The conversion of α-hydroxyisobutyric acid amide was 66.7%, the selectivity into methyl α-hydroxyisobutyrate was 98.1%, and the selectivity into formamide was 98.5%.

EXAMPLE 8

The same autoclave as used in Example 1 was charged with 10.3 g (0.1 mol) of α-hydroxyisobutyric acid amide, 32 g (1.0 mol) of methanol, and 2.8 g (0.05 mol) of calcium oxide, and then sealed.

Then, carbon monoxide was introduced under pressure of 40 atm, and agitation was started while heating.

When the temperature in the autoclave reached 100° C., carbon monoxide was introduced so as to maintain the reaction pressure at 40 atm, and the reaction was continued for 3 hours.

Then, the autoclave was cooled to 10° C., and the inner pressure was gradually lowered to atmospheric pressure. Thereafter the reaction product was taken out of the autoclave and analyzed.

The conversion of α-hydroxyisobutyric acid amide was 7.3%, the selectivity into methyl α-hydroxyisobutyrate was 5.1%, and the selectivity into formamide was 93.5%.

What is claimed is:

1. A process for production of carboxylic acid ester and formamide which comprises reacting carboxylic acid amide and formic acid ester in the presence of an alkaline earth metal oxide catalyst.

2. A process for production of carboxylic acid ester and formamide which comprises reacting carboxylic acid amide, alcohol and carbon monoxide in the presence of an alkaline earth metal oxide catalyst.

3. The process as claimed in claim 1 or 2, wherein the alkaline earth metal oxide catalyst is at least one selected from magnesium, calcium, strontium and barium oxides.

4. The process as claimed in claim 1, wherein the alkaline earth metal oxide catalyst is calcium oxide or barium oxide.

5. The process as claimed in claim 2, wherein the alkaline earth metal oxide catalyst is calcium oxide or barium oxide.

6. The process as claimed in claim 1 or 2, wherein the carboxylic acid amide is aliphatic carboxylic acid amide, aromatic carboxylic acid amide, α-hydroxycarboxylic acid amide, or α-aminocarboxylic acid amide.

7. The process as claimed in claim 1 or 2, wherein the carboxylic acid amide is at least one compound selected from the group consisting of acetamide, lactic acid amide, acrylic acid amide, methacrylic acid amide, benzamide, α-hydroxyisobutyric acid amide, and alanineamide.

8. The process as claimed in claim 1, wherein the formic acid ester is at least one selected from the group consisting of methyl formate, ethyl formate, propyl formate, isopropyl formate, n-butyl formate, sec-butyl formate, and n-pentyl formate.

9. The process as claimed in claim 4, wherein the formic acid ester is methyl formate.

10. The process as claimed in claim 2, wherein the alcohol is an aliphatic alcohol having 1 to 10 carbon atoms.

11. The process as claimed in claim 2, wherein the alcohol is at least one compound selected from the group consisting of methanol, ethanol, 1-propanol, 2-propanol, 1-butanol, 2-butanol, and 1-pentanol.

12. The process as claimed in claim 5, wherein the alcohol is methanol.

13. The process as claimed in claim 1 or 2, wherein the amount of the alkaline earth metal oxide catalyst is 0.001 to 0.3 mol per mol of the carboxylic acid amide.

14. The process as claimed in claim 1 or 2, wherein the amount of the alkaline earth metal oxide catalyst is 0.003 to 0.2 mol per mol of the carboxylic acid amide.

* * * * *